United States Patent [19]

Mack, II et al.

[11] Patent Number: 4,876,207

[45] Date of Patent: Oct. 24, 1989

[54] COMPOSITIONS FOR THE DETECTION OF HIGH LEVELS OF HYDROGEN PEROXIDE

[75] Inventors: Arthur R. Mack, II, Penn Yan; John W. H. Sutherland, Jr., Rochester, both of N.Y.

[73] Assignee: Eastman Kodak Company, Rochester, N.Y.

[21] Appl. No.: 156,129

[22] Filed: Feb. 16, 1988

[51] Int. Cl.[4] .............................................. G01N 33/00
[52] U.S. Cl. ...................................... 436/135; 435/14; 436/14; 252/186.2; 252/186.29
[58] Field of Search ..................... 435/4, 10, 11, 12, 14, 435/22, 25, 26, 28, 171, 189, 190, 192, 805, 810, 911; 436/71, 95, 97, 99, 169, 170, 163, 175, 903, 135, 63, 171; 422/55–58; 252/186.1, 186.2, 186.25, 186.28, 188.1, 408.1

[56] References Cited

U.S. PATENT DOCUMENTS

| Re. 32,016 | 10/1985 | Esders et al. | 435/28 |
| 4,554,249 | 11/1985 | Kosaka et al. | 435/10 |
| 4,578,245 | 3/1986 | Arai et al. | 435/14 |
| 4,587,100 | 5/1986 | Amano et al. | 435/11 |
| 4,604,347 | 8/1986 | Arai et al. | 435/26 |
| 4,637,978 | 1/1987 | Dappen | 435/28 |
| 4,732,736 | 3/1988 | Kobayashi et al. | 435/28 |

FOREIGN PATENT DOCUMENTS

| 0052564 | 3/1983 | Japan . |
| 0929569 | 5/1982 | U.S.S.R. . |
| 1142800 | 2/1985 | U.S.S.R. . |

OTHER PUBLICATIONS

Kodak Ektachem Clinical Chemistry Slides for Glucose Assay, Eastman Kodak Company, 1985, Publication No. MP3-12.

Primary Examiner—Barry S. Richman
Assistant Examiner—T. J. Wallen
Attorney, Agent, or Firm—John R. Everett

[57] ABSTRACT

A dye development composition comprising 1,10-phenanthroline and 1,7-dihydroxynaphthalene is disclosed for use in assaying high levels of hydrogen peroxide.

14 Claims, 2 Drawing Sheets

COMPOSITIONS FOR THE DETECTION OF HIGH LEVELS OF HYDROGEN PEROXIDE

FIELD OF THE INVENTION

The present invention relates to analytical chemistry. In particular it relates to a composition for the determination of high levels of hydrogen peroxide and glucose and to methods and dry analytical elements in which the composition is used.

BACKGROUND OF THE INVENTION

The detection and quantitative determination of hydrogen peroxide and of compounds yielding hydrogen peroxides such as glucose are of importance in many areas. Known compositions for detecting and/or quantifying hydrogen peroxide generally comprise a substance having peroxidative activity and a material which undergoes a detectable change (generally a color change) in the presence of hydrogen peroxide and the peroxidative substance.

It would be useful, and in some cases necessary, for a diabetic to maintain better quantitative control over blood glucose levels. One strategy contemplates providing diabetics with (1) a dry analytical element comprising a glucose test slide containing all of the reagents needed to determine glucose blood levels and (2) a small pocket reflectometer which uses a light emitting diode (LED) as a light source. This strategy faces several problems.

First, many of the prior art methods for detection of hydrogen peroxide are not useful in determining glucose. This is because glucose is present in relatively high levels in blood serum. Thus glucose generates large amounts of hydrogen peroxide. Correspondingly large amounts of dye are produced. The test elements usually become optically dense resulting in high reflection densities. An accurate reading of very dense test elements requires a good reflectometer. Such tests are not available for home use by diabetics because of the high cost of good reflectometers.

Secondly, commercially available light emitting diodes vary widely in their light intensity versus wavelength profiles. This variation could lead to considerable calibration difficulties.

Thirdly, hemoglobin interference up to 620 nanometers in some tests necessitates the use of a white rug or dye to mask the hemoglobin which further drives up test costs.

Thus in order to make available a reasonably accurate home testing kit for diabetics the above problems have to be overcome. More specifically, the problems are to provide a dye development composition that (1) does not develop too high a reflection density in the face of high levels of blood glucose and (2) develops a dye having a broad absorption band beyond 620 nanometers to allow reflection density readings beyond 620 nanometers thereby avoiding hemoglobin interference and overcoming problems of light emittent diode variation.

SUMMARY OF THE INVENTION

The present invention provides a dye development composition comprising 1,10-phenanthroline and 1,7-dihydroxynaphthalene.

This composition does not develop high reflection densities ($D_r$) and the developed dye has a broad absorption band beyond 620 nanometers. The reaction between the two components of the composition is not understood and is completely unexpected. Glucose, and other $H_2O_2$ generating analytes in which the composition is used, show good agreement between predicted and actual levels of glucose and hydrogen peroxide at high levels of glucose and hydrogen peroxide. Also hemoglobin interference and calibration problems with LEDs are avoided.

In a preferred embodiment the invention provides a multilayer analytical element for determining hydrogen peroxide levels in aqueous fluids comprising a support bearing one or more reagent layer(s) comprising a peroxidase active substance, 1,10-phenanthroline and 1,7-dihydroxynaphthalene; wherein the peroxidase active substance and 1,10-phenanthroline and 1,7-dihydroxynaphthalene are in the same or different reagent layers.

DETAILS OF THE INVENTION

Figure 1:
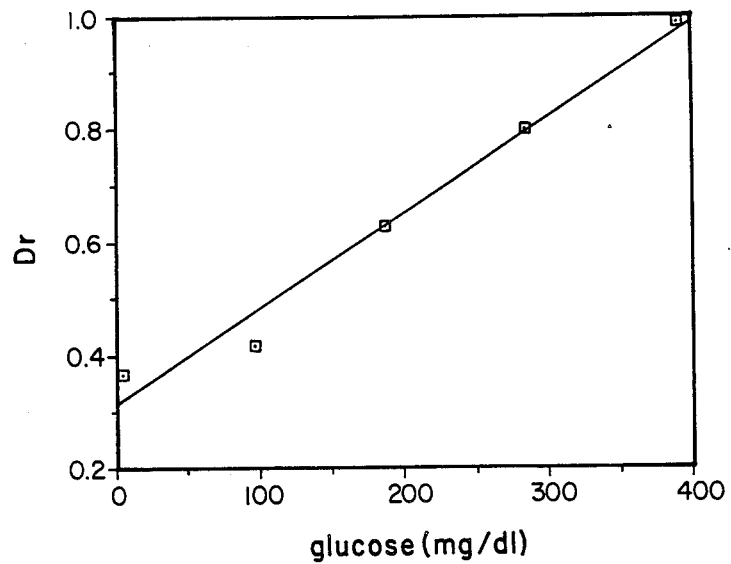
FIGS. 1 and 2 show the plotted data of example 1 relating to the increase in reflection density with increases in the hydrogen peroxide and glucose levels.

The dye development composition of the present invention provides a qualitative and quantitative determination of $H_2O_2$ in aqueous liquids. Therefore, the assay can be used in assays for glucose, creatine kinase, cholesterol, ethanol, triglyceride, lipase, lactate dehydrogenase, etc. The invention can be used to assay biological fluids of either animals or humans, but preferably of humans. Such fluids include, but are not limited to, whole blood, plasma, sera, lymph, bile, urine, spinal fluid, sputum, perspiration and the like as well as stool secretions. It is also possible to assay fluid preparations of human or animal tissue such as skeletal muscle, heart, kidney, lungs, brains, bone marrow, skin and the like.

Both 1,10-phenanthroline and 1,7-dihydroxynaphthalene are known compounds and are readily available. Combining those compounds in a single composition is, however, novel. In the presence of $H_2O_2$ and a material having peroxidase activity and a pH of 5 to 10, the composition develops a dye.

A peroxidase is an enzyme which will catalyze a rection wherein hydrogen peroxide oxidizes another substance. The peroxidases are generally conjugated proteins containing iron porphyrin. Peroxidase occurs in horseradish, potatoes, figtree sap and turnips (plant peroxidase); in milk (lacto peroxidase); and in white blood corpuscles (verdo peroxidase); also it occurs in microorganisms and may be produced by fermentation. Certain synthetic peroxidases, such as those disclosed by Theorell and Maehly in Acta Chem. Scand, Vol. 4, pages 422–434 (1950), are also satisfactory for use in $H_2O_2$ detection systems. Less satisfactory are such materials as hemin, methemoglobin, oxyhemoglobin, hemoglobin, hemochromogen, alkaline hematin, hemin derivatives, and certain other materials which demonstrate peroxidative or peroxidase-like activity, namely the ability to catalyze the oxidation of another substance by means of hydrogen peroxide and other peroxides.

Those skilled in the art of analytical chemistry will understand that the relative amounts of each component chemical included in the composition to conduct an assay for a particular analyte will depend upon the expected concentration of the analyte. Based upon such expected concentration, each component is added to obtain the necessary stoichiometric reactions. However, useful ranges are given for the analytical element exemplified herein.

Substantially any buffer is a suitable candidate for establishing the desired pH. Useful buffers will, or course, establish the pH in the range 5 to 10 which is conducive to the occurrence of dye development reaction while not inhibiting the reaction. We have found that useful buffers include carbonate buffers such as sodium and potassium carbonate, borate, buffers such as sodium and potassium borate, citrate, phosphate such as $NaH_2PO_4$ and glutarate buffers and the tris materials such as tris(hydroxymethyl)aminomethane. Some of these materials buffer the reagent composition to a range of between about 5 and 10 which is a useful pH range for detecting blood serum components using the particular indicator described herein in coupled enzymatic reaction sequences useful in the assay of glucose using glucose oxidase to produce hydrogen peroxide.

The compositions described herein may be incorporated into bibulous or absorbent analytical elements of the type well known in the art.

The novel dye development composition of the present invention can be incorporated into fibrous filter paper type testing materials or multilayered analytical elements of the type described in U.S. Pat. No. 3,992,158 of E. P. Przybylowicz and A. G. Millikan.

The simple fibrous element can be composed of an absorbent carrier material, for example, a thin sheet of a self-supporting absorbent or bibulous material, such as filter paper or strips, which contains the analytical composition of this invention. The element can be divided into two or more discrete zones with different reagents incorporated into individual zones of the carrier material. Such elements are known in the art as test strips, diagnostic elements, dip sticks or diagnostic agents.

Useful absorbent carrier materials are insoluble and maintain their structural integrity when exposed to water or biological fluids such as whole blood or serum. Useful elements can be prepared from paper, porous particulate structures, porous polymeric films, cellulose, glass fibers, woven and nonwoven fabrics (synthetic and nonsynthetic) and the like. Useful materials and procedures for making such elements are well known in the art as exemplified in U.S. Pat. Nos. 3,092,465; 3,802,842; 3,915,647; 3,917,453; 3,936,357; 4,248,829; 4,255,384; 4,270,920; and 4,312,834.

Preferably, the absorbent carrier material of the above analytical element contains a porous spreading zone. This zone can be self-supporting (that is, composed of a material rigid enough to maintain its integrity), but preferably it is carried on a separate support. Such a support can be any suitable dimensionally stable, and preferably, nonporous and transparent (that is, radiation transmissive) material which transmits electromagnetic radiation of a wavelength between about 200 and about 900 nm. A support of choice for a particular element should be compatible with the reflectance spectroscopy mode of colorimetry. Useful supports can be prepared from paper, polystyrene, polyesters, polycarbonates, cellulose esters and others known in the art.

The porous spreading zone can be prepared from any suitable fibrous or non-fibrous material or mixtures of either or both. The void volume and average pore size of this zone can be varied depending upon the use intended.

Useful spreading zones can be prepared using fibrous materials, either mixed with a suitable binder material or woven into a fabric, as described in U.S. Pat. No. 4,292,272, polymeric compositions or particulate materials, for example, blush polymers as described in U.S. Pat. No. 3,992,158, beads bound together with or without binding adhesives, as described in U.S. Pat. Nos. 4,258,001 and 4,430,436 and Japanese Patent Publication No. 57(1982)-101760. It is desirable that the spreading zone be isotropically porous, meaning that the porosity is the same in each direction in the zone as caused by interconnected spaces or pores between particles, fibers or polymeric strands.

The dry element can have two or more discrete zones, either in the same layer or superimposed. At least one of the zones is preferably a porous spreading zone or a combination spreading/reagent zone. The other zones can be reagent zones or registration zones as those zones are known in the art, additional spreading zones, radiation-blocking or filter zones, subbing zones or barrier zones. The zones are generally in fluid contact with each other, meaning that fluids, reagents and reaction products (for example, color dyes) can pass or be transported between superposed regions of adjacent zones. In other words, when the element is contacted with fluid, all reagents of the analytical composition of this invention become mixed and can readily move within the element as a composition. Preferably a multilayer element is used in which each zone is a separately coated layer, although two or more zones can be separate areas in a single layer of the element. Besides the references noted above, suitable element components are described also in U.S. Pat. Nos. 4,042,335; 4,132,528 and 4,144,306.

The preferred multilayer element is placed in use by applying to the element a sample of liquid under analysis. Typically, an element will be formed such that an applied sample will contact a spreading layer, or a combination spreading/reagent layer, prior to the reagent layer and will first contact such spreading layer at its surface furthest removed from such reagent layer. Because analytical accuracy of the present elements is not substantially diminished by variations in the volume of applied samples, sample application by hand or machine is acceptable. For reasons of convenience in detecting an analytical result, however, reasonable consistency in sample volume may be desirable.

In a typical analytical procedure using the elements, which could be manual or automated, the element is taken from a supply roll, chip packet or other source and positioned to receive a free drop, contact spot or other form of liquid sample, such as from an appropriate dispenser. After sample application, and desirably after the liquid sample has been taken up by a spreading layer, the element is exposed to any conditioning, such as heating, humidification or the like, that may be desirable to quicken or otherwise facilitate obtaining any test result. To avoid migration of a developed dye spot after reaction of a sample solution with the reagent composition of the invention, the reagent or registration zone or layer of the element may include a mordant such as polystyrene co-meta and poly(styrene-com+p-N-vinyl-benzyl-N-benzyl-N,N-dimethyl ammonium chloride (60,40)-co-divinylbenzene (49.5; 49.5; 1).

After the analytical result is obtained as a detectable change, it is measured, usually by passing the element through a zone in which suitable apparatus for reflection or transmission spectrophotometry is provided. Such apparatus would serve to direct a beam of energy, such as light, through the support and the reagent layer. The light would then be reflected, such as from an opacifying agent in the spreading or a radiation-blocking layer in the element, back to a detecting means or would pass through the element to a detector, in the case of transmission detection. In a preferred mode, the analytical result is detected in a region of the element totally within the region in which such result is produced. Generally, electromagnetic radiation in the range of from about 400 to about 700 nm has been found useful for such measurements, although any radiation to which the element is permeable and which is capable of quantifying the detectable change produced in the element can be used. Various calibration techniques can be used to provide a control for the analysis. As one example, a sample of analyte standard solution can be applied adjacent to the area where the drop of sample is placed in order to permit the use of differential measurements in the analysis.

The elements of this invention can also contain one or more other addenda commonly put in the elements for various manufacturing or operational advantages. Such addends include surfactants, buffers, solvents, hardeners and other materials known in the art.

The following example demonstrates the operation of dry multilayer analytical elements in which the dye development composition of the invention are incorporated for the determnination of $H_2O_2$ and glucose.

EXAMPLE 1

Materials
1,10-phenanthroline (1,10-P)
1,7-dihydroxynaphthalene (DHN)
glucose oxidase (GOD)
horseradish peroxidase (HRP)
$NaH_2PO_4$
Polyvinyl pyrrolidone-K90 from GAF
a non ionic flurosurfactant
poly(styrene-co-m+p-N-vinylbenzyl-M-benzylN,N-dimethyl ammonium chloride (60,40)-co-divinylbenzene (49.5; 49.5; 1)
Handcoatings were prepared as follows.

Eighty mg each of 1,10-phenanthroline and 1,7-dihydroxynaphthalene and 100 mg PVP were dissolved in 5.5 ml methanol. Approximately 50 µl of 50% Zonyl FSN and 0.5 ml of 17.7% PVP were added to the latter solution. The resulting mixture was handcoated over a gel pad (10 g/m$^2$) on a 7 mil thick transparent polyester support, and air dried to form a first reagent layer.

Three hundred mg $NaH_2PO_4$ 250 mg PVP were dissolved in 12 mL water. The pH was adjusted to 6.0 with dilute NaOH. HRP (12 mg at 275 units/mg) and GOD (96 mg at 37 units/mg) were added. When these enzymes dissolved, 50 µl of 50% Zonyl FSN and 8.25 g of poly(m+p-vinyltoluene-co-p-t-butylstyreneco-methacrylic acid) beads were added. This mixture was coated over the first reagent layer, described above, and air dried. The latter layer was a combination spreading and reagent layer.

The resulting element had the layer arrangement depicted below:

| | Element Format | g/m$^2$ | Example of Useful Range g/m$^2$ |
|---|---|---|---|
| Spreading/Reagent Layer | $NaH_2PO_4$ | 3.2 | 1–8 |
| | Polyvinyl pyrrolidone-K90 Reagent | 2.7 | 2–5 |
| | Peroxidase | 36,000 µ/m$^2$ | 10,000–50,000 |
| | Glucose Oxidase | 38,000 µ/m$^2$ | 10,000–50,000 |
| | Non Ionic Surfactant | 0.3 | .05–.5 |
| | Beads | 89 | 60–150 |
| Reagent Layer | 1,10-phenanthroline | 0.9 | .5–1.5 |
| | 1,7-dihydroxy naphthalene | 0.9 | .5–1.5 |
| | Polyvinyl pyrrolidone-K90 | 1.08 | 1–5 |
| | Poly(styrene-co-m + p-N—vinylbenzyl-N—benzyl-N,N—dimethyl ammonium chloride (60,40)-co-divinylbenzene (49.5; 49.5; 1) | 0.9 | .1–3 |
| | Non Ionic Surfactant | 0.25 | .05–5 |
| | Gel Pad | 10.8 | 5–50 |
| | Polyester Support | | |

The above handcoated element was tested with 1) a series of serum samples containing known concentrations of glucose and 2) a series of aqueous solutions containing known concentrations of $H_2O_2$. Webs of this element were spotted with 10 µl of each liquid. Stabilized reflectance density measurements were made with a photometer. In all cases measurements were made 5 minutes after spotting except the data in Table 4, infra, is based on measurements made after 2 minutes and 40 seconds.

The reflectance density measurements ($D_r$) for the glucose spiked serum samples were plotted. A straight line curve was was fitted to the plotted values. See FIG. 1. Table 1 below compares the actual glucose concentrations to predicted concentrations predicted by the curve of FIG. 1. Good agreement belween actual and predicted concentrations was achieved at concentrations of above 180 mg/dl of glucose. This data shows that the element of this invention can be used to determine high glucose levels (above 180 mg/dl) in serum at a wavelength at which hemoglobin does not absorb (hemoglobin absorbs at wavelengths up to 620 nm). The data also shows that the reflectance density of the samples were not too high to cause errors from stray light.

TABLE 1

| Glucose (mg/dl) | $D_r$ (590 nm) | Predicted Concentration (mg/dl) |
| --- | --- | --- |
| 5.4 | .37 | 32 |
| 97 | .42 | 62 |
| 187 | .63 | 185 |
| 284 | .80 | 285 |
| 391 | .99 | 397 |

Figure 2:
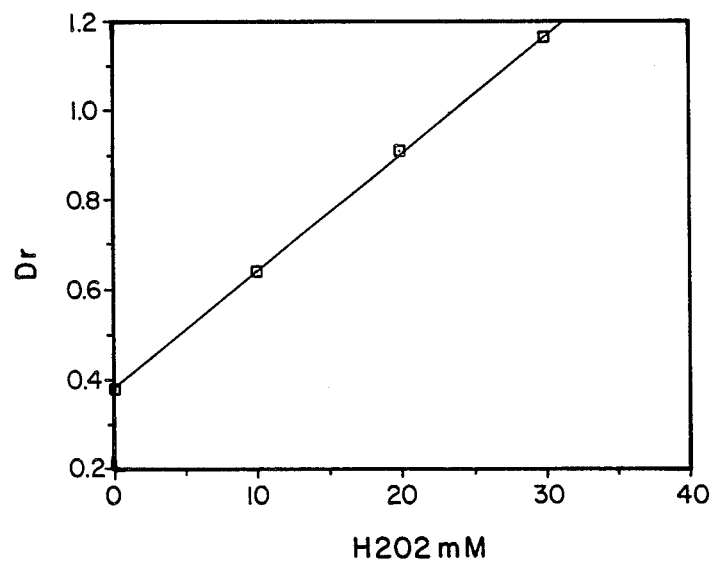

FIG. 2 is a curve which was fitted to the actual reflectance reading for the $H_2O_2$ spiked aqueous samples. Table 2 is a comparison between actual and predicted concentrations. The data of table 2 is consistent with the conclusion reached relative to glucose determinations with the element of the invention. However, the agreement between actual and predicted concentrations of $H_2O_2$ is good throughout the measured range.

TABLE 2

| $H_2O_2$ (mM) | $D_r$ (590 nm) | Predicted Concentration (mM) |
| --- | --- | --- |
| 0 | .38 | 0 |
| 10 | .64 | 9.9 |
| 20 | .91 | 20.3 |
| 30 | 1.16 | 29.9 |

COMPARATIVE EXAMPLE

To demonstrate the improved measurement of high glucose levels using the compositions and elements made possible by the present invention, a comparison was made between the element used in example 1 containing the color developing composition of the present invention and the same element containing a prior art color developer composition of the type used, for example, in clinical chemistry slides provided heretofore by Eastman Kodak Company. The latter element is referred to hereinafter as the prior art element. The coupler was the same in both elements. The two different elements were spotted as in example 1 with the glucose spiked serum solutions and $H_2O_2$ spiked aqueous solutions.

Figure 3:
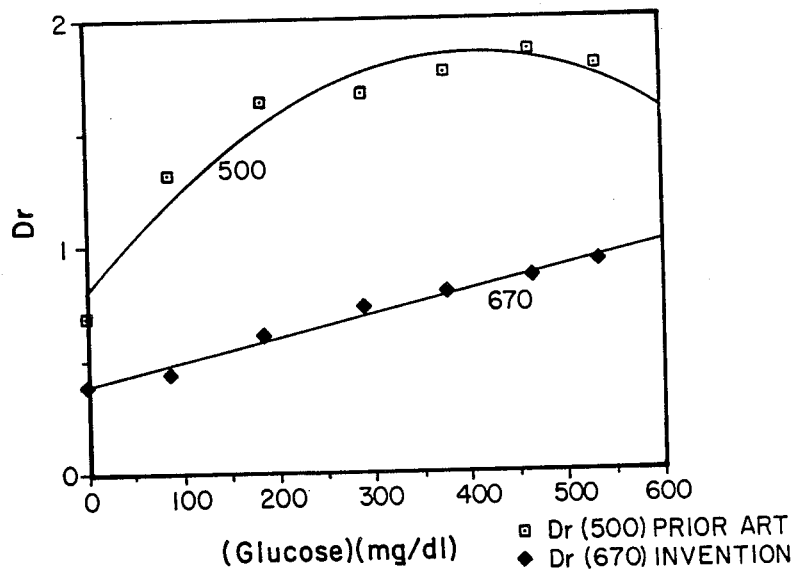
FIGS. 3 and 4 are curves comparing the reflection density of a prior art dye development composition with the dye development composition of the present invention.

Reflectance density ($D_r$) measurements were then made as in example 1 except measurements were made at 500 nm for the prior art element because peak absorption was observed at that wavelength for the developed dye. The measurements were plotted and curves fitted to the data as in example 1. FIG. 3 is the result. A straight line was obtained with the element of the invention consistent with the example. A curve having a peak was obtained for the prior art element. Also the readings on the prior art element reached a $D_r$ of about 1.8 at glucose levels of 400 mg/dl compared to a $D_r$ of about 0.8 for the element of the invention.

The effect of high $D_r$ on agreement between predicted and actual glucose concentrations is shown in Table 3. Much better agreement is obviously achieved with the present invention at high glucose levels (above 400 mg/dl) for which the present invention is targeted.

TABLE 3

| Actual Conc. (mg/dl) | Present Invention 1,10-Phenanthroline and 1,7-dihydroxynaphthalene | | Prior Art 4-Aminoantipyrene and 1,7-dihydroxynaphthalene | |
| --- | --- | --- | --- | --- |
| | $D_r$(670 nm) | Predicted Conc. (mg/dl) | $D_r$(500 nm) | Predicted Conc. (mg/dl) |
| 0 | .39 | 0 | .69 | −20 |
| 86 | .44 | 50 | 1.32 | 119 |
| 185 | .6 | 210 | 1.63 | 221 |
| 290 | .73 | 340 | 1.67 | 240 |
| 375 | .79 | 400 | 1.76 | 286 |
| 464 | .86 | 470 | 1.86 | 405 |
| 533 | .92 | 530 | 1.79 | —* |

*This value not predictable because $D_r$ versus concentration curve (of the prior art) passes through a maximum. See FIG. 3.

Figure 4:
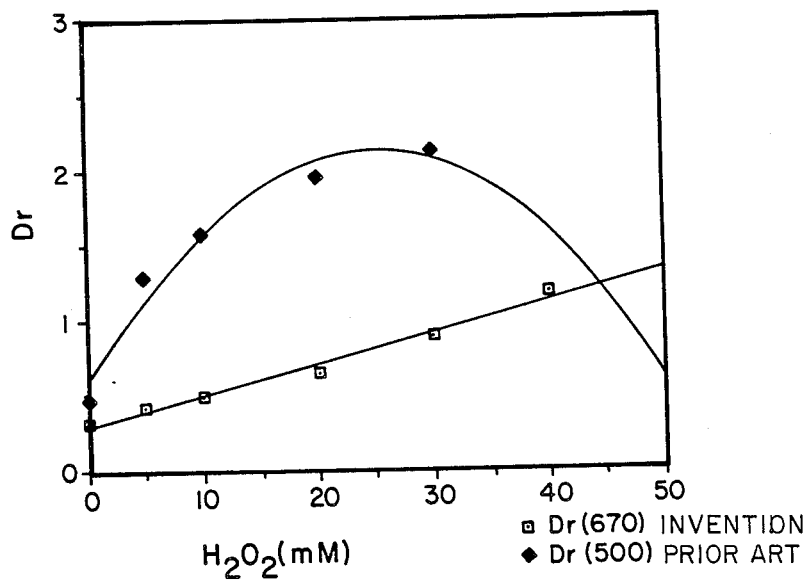

The same comparisons were made using the $H_2O_2$ spiked aqueous samples. The observed data of FIG. 4 and table 4 supports the above conclusions that for high concentrations of $H_2O_2$ the high $D_r$ values obtained with prior art color developer leads to less agreement between predicted and actual $H_2O_2$ concentrations than the color developer composition of the present invention.

TABLE 4

| Actual Conc. mg/dl | Prior Art 4-Aminoantipyrene 1,7-dihydroxynaphthalene | | Present Invention 1,10-Phenanthroline 1,7-dihydroxynaphthalene | |
| --- | --- | --- | --- | --- |
| | $D_r$(500 nm) | Predicted Conc. mg/dl | $D_r$(670 nm) | Predicted Conc. mg/dl |
| 0 | .46 | −15.3 | 0.33 | 25.2 |
| 90 | 1.29 | 122.4 | 0.43 | 113.4 |
| 180 | 1.57 | 180 | 0.49 | 165.6 |
| 360 | 1.95 | 306 | 0.65 | 306 |
| 540 | 2.12 | 468 | 0.89 | 522 |
| 720 | —* | —* | 1.18 | 774 |

*This value not predictable because $D_r$ versus concentration curve (of the prior art) passes through a maximum. See FIG. 3.

The invention has been described in detail with particular reference to preferred embodiments thereof, but it will be understood that variations and modifications can be effected within the spirit and scope of the invention.

We claim:

1. A dye development composition comprising 1,10-phenanthroline and 1,7-dihydroxynaphthalene.

2. The composition of claim 1 also comprising a peroxidase active material.

3. The composition of claim 1 or 2 wherein each chemical component is present in a sufficient concentration to at least react stoichiometrically with an expected concentration of an analyte.

4. A method for determining hydrogen peroxide levels in aqueous solution having a pH comprising the steps of:
  (a) adjusting the pH of the aqueous solution between 5 and 10;
  (b) providing a peroxidase active material;
  (c) providing a composition comprising 1,10-phenanthroline and 1,7-dihydroxynaphthalene;
  (d) combining (a), (b) and (c) to form a dye; and
  (e) determining the hydrogen peroxide level photometrically from the dye.

5. The method of claim 4 wherein the photometric determinations are carried out at wavelengths greater than 620 nanometers.

6. The method of claim 4 wherein the photometric determination is carried out at about 670 nanometers.

7. A method for determining glucose levels in an aqueous solution having a pH comprising the steps of:
   (a) adjusting the pH of the aqueous solution between 5 and 10;
   (b) providing a peroxidase active material;
   (c) providing a composition comprising 1,10-phenanthroline and 1,7-dihydroxynaphthalene;
   (d) combining a), b) and c) to form a dye; and
   (e) determining the glucose level photometrically from the dye.

8. The method as in claim 4 or 7 wherein the aqueous solution is blood serum.

9. An analytical element for determining hydrogen peroxide levels in aqueous fluids comprising an absorbent material containing a peroxidase active material; 1,10-phenanthroline and 1,7-dihydroxynaphthalene.

10. A multilayer analytical element for determination of hydrogen peroxide in an aqueous medium comprising a support bearing in the following order;
   (a) one or more reagent layer(s) comprising a peroxidase active substance, 1,10-phenanthroline and 1,7-dihydroxynaphthalene; wherein the peroxidase active substance and 1,10-phenanthroline and 1,7-dihydroxynaphthalene are in the same reagent layers; and
   (b) a spreading layer in fluid contact with the reagent layer(s).

11. The element of claim 10 comprising two or more reagent layers wherein one of the reagent layers comprises a material which oxidizes glucose to produce hydrogen peroxide and the second reagent layer comprises 1,10-phenanthroline and 1,7-dihydroxynaphthalene.

12. The element of claim 10 comprising a combination spreading and reagent layer in contact with a second reagent layer.

13. The element of claim 12 wherein a) the spreading and reagent layer comprises from 1 to 8 $g/m^2$ of $NaH_2PO_4$; from 2 to 5 $g/m^2$ of polyvinyl pyrrolidone-K90 reagent; from 10,000 to 50,000 I.U. of peroxidase; from 10,000 to 50,000 I.U. of glucose oxidase and from 0.05 to 0.5 $g/m^2$ of a non ionic surfactant; and (b) the reagent layer comprises from 0.5 to 1.5 $g/m^2$ 1,10-phenanthroline; from 0.5 to 1.5 $g/m^2$ 1,7-dihydroxynaphthalene; from 1 to 5 $g/m^2$ of polyvinyl pyrrolidone-K90 reagent; from 0.1 to 3 $g/m^2$ of poly(styrene-co-m+p-N-vinyl-benzyl-N-benzyl-N,N-dimethyl ammonium chloride (60,40)-co-divinylbenzene (49.5; 49.5; 1) and from 0.05 to $-5$ $g/m^2$ of a non ionic surfactant.

14. A multilayer analytical element for determination of hydrogen peroxide in an aqueous medium comprising a support bearing in the following order;
   (a) one or more reagent layer(s) comprising a peroxides active substance, 1,10-phenanthroline and 1,7-dihydroxynaphthalene; wherein the peroxidase active substance and 1,10-phenanthroline and 1,7-dihydroxynaphthalene are in different reagent layers; and
   (b) a spreading layer in fluid contact with the reagent layer(s).

* * * * *

UNITED STATES PATENT AND TRADEMARK OFFICE
CERTIFICATE OF CORRECTION

PATENT NO. : 4,876,207

DATED : October 24, 1989

INVENTOR(S) : Arthur R. Mack II

It is certified that error appears in the above-identified patent and that said Letters Patent is hereby corrected as shown below:

Col. 10, line 24, the part reading

"ides active"

should read

--idase active--.

Signed and Sealed this

Twenty-fifth Day of June, 1991

Attest:

HARRY F. MANBECK, JR.

*Attesting Officer*  *Commissioner of Patents and Trademarks*